United States Patent [19]
Griffin et al.

[11] 3,985,026
[45] Oct. 12, 1976

[54] SURFACE COATING TEST APPARATUS

[75] Inventors: Lawrence C. Griffin, Toledo; Homer D. F. Peters, Sylvania; Douglas E. Smith, Toledo, all of Ohio

[73] Assignee: Owens-Illinois, Inc., Toledo, Ohio

[22] Filed: Apr. 4, 1975

[21] Appl. No.: 565,206

[52] U.S. Cl. .................................. 73/150 R; 73/7
[51] Int. Cl.² .................. G01N 3/56; G01N 3/04
[58] Field of Search .................. 73/7, 9, 103, 150 R; 65/29; 269/141, 216, 225; 279/1 H

[56] References Cited
UNITED STATES PATENTS

| | | | |
|---|---|---|---|
| 2,530,257 | 11/1950 | Marcus | 73/150 |
| 2,714,755 | 8/1955 | Wright | 269/141 X |
| 2,976,034 | 3/1961 | Hiatt, Sr. | 269/225 X |
| 3,033,019 | 5/1962 | Oliver | 73/9 |
| 3,323,889 | 6/1967 | Carl et al. | 65/60 |
| 3,412,605 | 11/1968 | Oehme et al. | 73/7 X |
| 3,631,709 | 1/1972 | Smith et al. | 73/3 |

Primary Examiner—Richard C. Queisser
Assistant Examiner—John S. Appleman
Attorney, Agent, or Firm—S. M. McLary; E. J. Holler

[57] ABSTRACT

Apparatus for testing a surface coating on a glass container. In this apparatus, a glass container is chucked in place on a movable carriage. A second glass container is held in a fixed position above and touching the first glass container. A load of a pre-determined magnitude is then applied normal to the second glass container, the load thereby being transmitted to the first glass container. The carriage is moved to cause the two glass containers to translate relative to one another. The force required to move the carriage is transmitted through a load cell which gives an output signal indicative of the force. The surface coatings applied to the glass containers should withstand a normal load of about one hundred pounds before breaking down and allowing the glass containers to scratch one another. If a scratch occurs during the test, the force required to move the carriage will increase and this may be easily seen.

6 Claims, 3 Drawing Figures

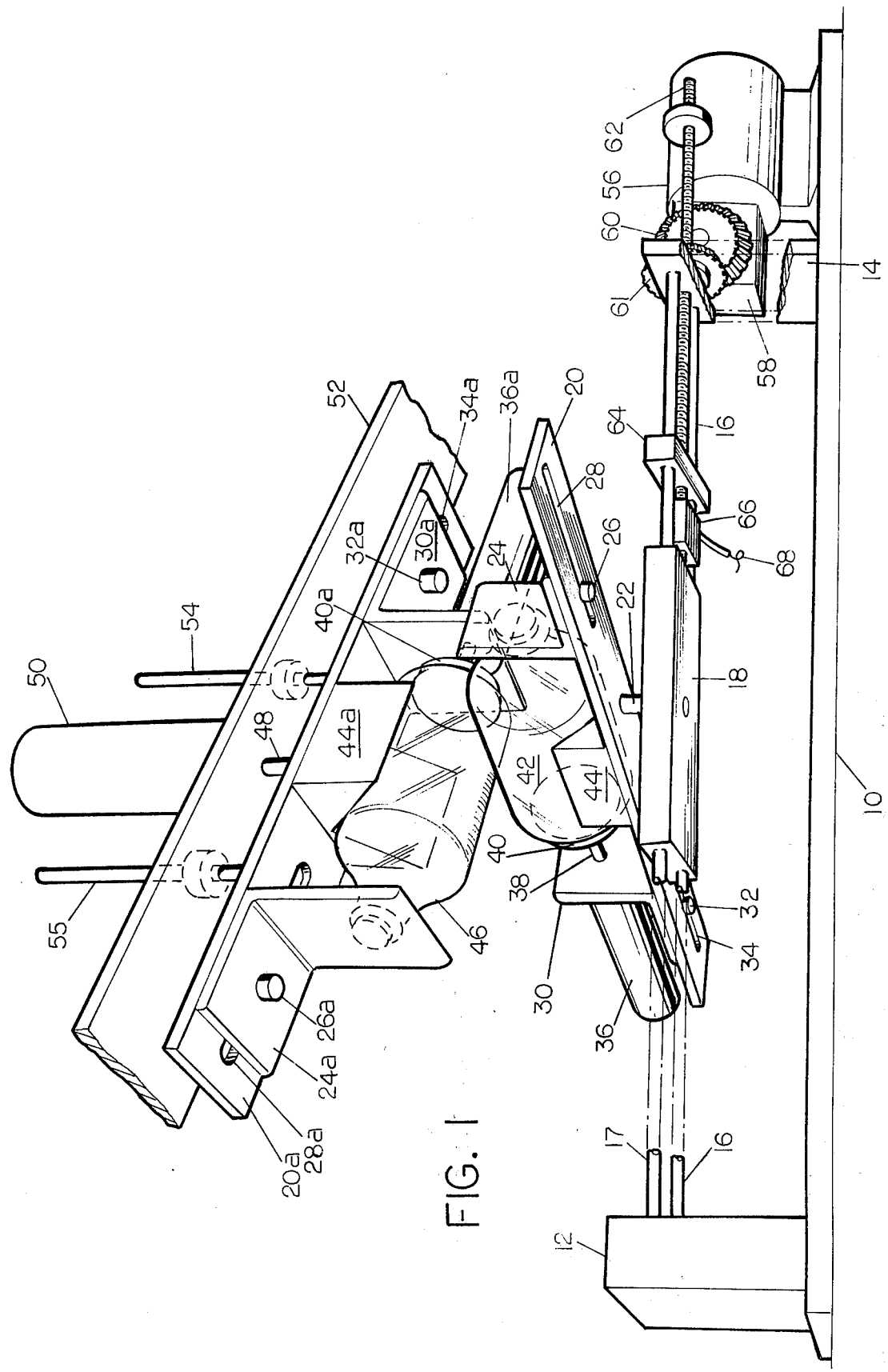

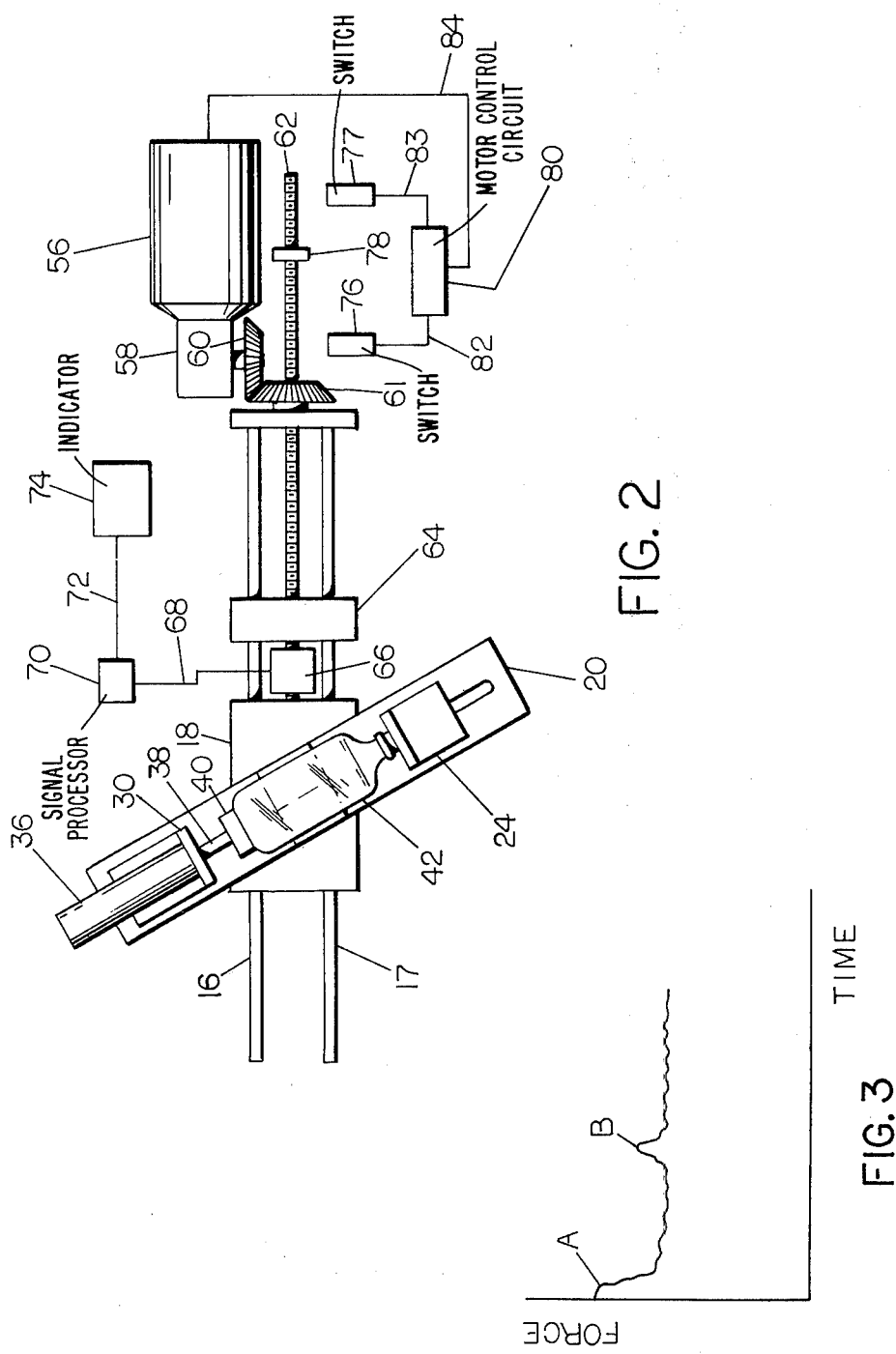

SURFACE COATING TEST APPARATUS

BACKGROUND OF THE INVENTION

This invention generally relates to apparatus for testing glass containers. More particularly, this invention relates to an apparatus for testing surface coatings on glass containers. Specifically, this invention relates to an apparatus for measuring the force required to move two glass containers relative to one another against an applied and known normally directed load.

Many glass containers are coated with a two-layer, transparent coating of a lubricious organic material over a metal oxide adhered to the glass surface. Such coatings tend to prevent glass containers from scratching one another when they are in contact. This scratch-preventative coating helps maintain the original high strength level of the glass containers. U.S. Pat. No. 3,323,889, the teachings of which are hereby incorporated by reference, teaches such a coating process and a technique for testing the coating. Basically, two coated glass containers should be capable of relative movement while in contact with one another without scratching while a normal load of about one hundred pounds is applied. The basic test procedure is sound, but has proven difficult to monitor in practice. An operator of the test must listen carefully to hear a scratch or must carefully examine each container after a test to see if any scratches were produced. In addition, no information relative to the coefficient of friction of various coatings could be obtained from these tests. The coefficient of friction can be of importance in mass handling situations such as bottle filling lines. We have invented a test apparatus which will measure the force required to move the glass containers relative to one another while a normal load is applied. With this force known, the coefficient of friction may be determined. In addition, when the coating under test fails and allows scratching, the force required to move the containers rises sharply, thus alerting a test operator to carefully examine that particular set of glass containers.

SUMMARY OF THE INVENTION

Our invention is an apparatus for testing a coating applied to glass containers for resistance to scratching when two glass containers are moved relative to one another while in contact. Mounted on a base are a pair of longitudinally separated support columns. A pair of transversely spaced-apart rails extend between and are held by the support columns. A carriage is slideably mounted on the rails. A first container chucking means for holding a glass container to be tested is carried by the carriage. A second container chucking means for holding a glass container is positioned above the first container chucking means. A force-applying means is positioned above the second container chucking means to apply a downward force on the second container chuck means normal thereto. A support means holds the force-applying means at a fixed location. A drive means moves the carriage along the rails. A sensing means generates a signal quantity which is representative of the force required to move the carriage.

BRIEF DESCRIPTION OF THE DRAWINGS

FIG. 1 is a perspective view from below, partially cut away, of the apparatus of the present invention;

FIG. 2 is a top plan view of the apparatus shown in FIG. 1 with the upper glass container and supporting structure removed; and FIG. 3 is a time vs. force chart illustrating typical test results using the apparatus of the present invention.

DETAILED DESCRIPTION OF THE DRAWINGS

The apparatus of the present invention may be seen in FIG. 1. The entire device is mounted upon a base or base plate 10. Longitudinally separated from one another on the base 10 are two main support columns 12 and 14. The support columns 12 and 14 are anchored to the base 10. Two rails 16 and 17 extend between the support columns 12 and 14. The rails 16 and 17 are transversely separated from one another and are parallel to one another. A carriage 18 is mounted on the rails 16 and 17 and is free to move along the rails 16 and 17. A lower support plate 20 is connected to and carried by the carriage 18 by a rotatable mounting post 22. The lower support plate 20 may be rotated relative to the carriage 18 by virtue of the mounting post 22, and may also be locked into a fixed position when desired. Carried by the lower support plate 20 is a clamp bracket 24. The clamp bracket 24 is held onto the lower support plate 20 by a bolt 26 which slides in a slot 28 formed in the support plate 20. A motor bracket 30 is also carried by the lower support plate 20. As was the case with the clamp bracket 24, the motor bracket 30 is secured to the support plate 20 by a bolt 32 which slides in a slot 34. A fluid motor 36 is attached to and carried by the motor bracket 30. The fluid motor 36 may be a gas-operated or air-operated cylinder or a hydraulic-operated cylinder. The fluid motor 36 includes an extensible operating rod 38 which carries on its end a clamp pad 40. The operating rod 38 is extended in normal operation to bring the clamp pad 40 into contact with the bottom or heel portion of a glass container 42 to be tested. The force exerted by the clamp pad 40 forces the upper or finish portion of the glass container 42 into contact with the clamp bracket 24 and thus holds the glass container 42 securely in a fixed location. A cradle 44 is also attached to and carried by the lower support plate 20. The cradle 44 further locates and locks the position of the glass container 42 on the lower support plate 20. The clamp bracket 24 and motor bracket 30 are adjustable in their respective slots 28 and 34 to allow clamping of glass containers 42 of differing sizes. In the most general sense, the clamp bracket 24, the support plate 20, motor bracket 30, fluid motor 36, and clamp pad 40, serve as a chucking means for the glass container 42. An upper support plate 20a is supported above the lower support plate 20. A chucking means substantially identical to that carried by the lower support plate 20 is also carried by the upper support plate 20a. Rather than describe the components again, components that are identical to those previously described with respect to the lower support plate 20 are given identical numbers with respect to the upper support plate 20a, with the suffix a added to these numerals. The chucking means carried by the upper support plate 20a carries and chucks in place a second glass container 46. The upper support plate 20a is carried by an operating rod 48 of a fluid motor 50. The fluid motor 50 is fixed in place on a horizontal upper support beam 52. The horizontal support beam 52 is held at a fixed elevation above the base 10 by vertical legs connected to the base 10. These vertical legs are not shown in FIG. 1.

The upper support plate 20a is further connected to the horizontal support beam 52 through two guide rails 54 and 55 which help control the vertical motion of the upper support plate 20a. The fluid motor 50 is pressurized to a known level such that the glass container 46 is pressed down upon the glass container 42 with a known load which is normal to the glass container 42. The driving power for this entire test apparatus is provided by an electrical motor 56 which is of the type that has an integrally attached gear head 58 that provides the output from the motor 56. The output from the gear head 58 is connected to an external gear set 60 and 61. The gears 60 and 61 are in mesh and will be driven by the motor 56. The gear 61 is attached to a threaded shaft 62. The threaded shaft 62 is threadably engaged in the support column 14 and extends between the rails 16 and 17 to a sliding drive block 64. The drive block 64 is separated from the carriage 18. A conventional load cell 66 is positioned between the drive block 64 and the carriage 18. When the shaft 62 is driven through the gear 61 and 60 from the motor 56, the drive block 64 will be pressed forward until the load cell 66 transmits the driving force imparted to the drive block 64 to the carriage 18. At this point, the carriage 18 will be moved to the left as seen in FIG. 1. During this time of motion, the force required to move the carriage 18 will be transmitted from the load cell 66 by an output conductor 68.

FIG. 2 shows a top view of the apparatus seen in FIG. 1 with the upper glass container 46 and its chucking means and fluid motor 50 removed. Note that the lower support plate 20 is positioned at an angle of approximately 45° with respect to the center line of the rails 16 and 17. This positioning is provided so that during an entire test cycle a clean surface will be presented between the two glass containers 42 and 46 during the motion of the glass container 42 to the left as seen in FIG. 2. That is, the glass container 46 is positioned above and in contact with the glass container 42 at right angles thereto. It may therefore be appreciated that the relative path of motion of the two glass containers 42 and 46 is a diagonal line along the length of the respective glass containers. The output conductor 68 from the load cell 66 is connected to a conventional load cell processing circuit 70. Such circuits are well known in the art and need not be described in detail. The output of the load cell processing circuit 70 is carried along a conductor 72 to an indicating means 74. The indicating means 74 may be a meter-type indicator which will show the amount of force required to move the carriage 18, or, preferably, may be a moving strip chart recorder which will give a continuous record of the force required to move the carriage 18 for an entire test. Such a chart is shown in FIG. 3 and will be discussed with respect to FIG. 3. Two switches 76 and 77 are positioned adjacent to the threaded shaft 62 and are spaced apart. The switches 76 and 77 determine the distance the carriage 18 will travel during any test. The switches are activated by a switch activator 78 which is carried by the threaded shaft 62. The switches 76 and 77 may be mechanical switches in which case the switch activator 78 would be a projection which would trip the mechanical levers of the switches 76 and 77; or the switches 76 and 77 may be proximity-type switches in which case the activator 78 could simply be a sufficient mass of material to activate the proximity sensing elements contained therein. The position or longitudinal separation of the switches 76 and 77 may be adjusted to compensate for glass containers 42 and 46 of varying lengths. It should be quite obvious that the length or height of any glass container tested will determine how far the carriage 18 need travel to ensure that the entire body surface of the glass container has been tested. Thus it is necessary to adjust the total length of travel of the carriage 18 for varying sizes of glass containers. The switches 76 and 77 are connected to a motor-control circuit 80 through respective conductors 82 and 83. In turn, the motor-control circuit 80 is connected to and controls the operation of the motor 56 through a conductor 84. At the beginning of the test, a start signal is introduced from the motor-control circuit 80 which is transmitted along the conductor 84 to begin the drive of the motor 56. As the motor 56 drives the threaded shaft 62, the switch actuator 78 will move along with the shaft 62 until it reaches the switch 76. At this time, the switch 76 will be activated which will transmit a signal along the conductor 82 to the motor-control circuit 80 which in turn will cause the motor 56 to be turned off terminating the test. The motor-control circuit 80 may include a fast reverse circuit which will allow the shaft 62 to return to its starting position at a speed faster than that at which the original test was conducted. When the shaft 62 has moved to its home position, the switch 77 will be actuated which will again cause the motor 56 to be shut off and will leave the apparatus in a state for the beginning of the next test. In this fast reverse cycle, of course, the load presented by the fluid motor 50 will have been removed so that there is no net force acting on the glass container 42 to impede its rapid return to the start or home position.

FIG. 3 is a typical strip chart recording from the indicating means 74 which shows a chart of force versus time for a test of a particular pair of glass containers. Note that at the beginning of the test at the point on the curve designated as A, the force is relatively high. This force indicates the coefficient of static friction which is a relatively high value thus requiring a relatively high force to overcome this factor. As the carriage 18 begins to move, the force drops down indicating that the coefficient of friction between the glass containers 46 and 42 has gone to the coefficient of kinetic or sliding friction, which is lower than the coefficient of static friction. If the coatings placed on the glass containers 46 and 42 were perfect, the chart would show a fairly steady level for the entire duration of the test. However, note the peak that occurs in the chart shown in FIG. 3, the peak being designated as B. This peak designated as B indicates that at some time during the test the coefficient of sliding friction increased significantly. This increase means that the coating on one or the other of the glass containers 42 or 46 broke down at some point during this test and thus undoubtedly created a scratch in one of the glass containers. Thus the chart shown in FIG. 3 allows a rapid determination of the coefficient of static friction from the formula $f_s = \mu_s N$ and the calculation of the coefficient of sliding friction or kinetic friction from the formula $f_k = \mu_k N$. Note that the $N$ in both cases is the normal force or the force which is applied to the upper glass container 46 through the fluid motor 50. As was previously pointed out, the prior art indicates that normal forces of approximately 100 pounds are the limit of the forces which the glass containers need pass to perform adequately in service. This device then allows rapid testing of glass containers to determine if the coating on these containers will pass this 100 pound level. In addition, by having an output chart of the actual test it is easy to see if the coating on the glass containers is spotty or if the coating is uniform as it should be. Furthermore, in the prior art, when similar devices were used for testing the coatings it was necessary to listen carefully to determine if the glass containers scratched one another or to examine the glass containers very carefully after each test to determine if the coatings have broken down to the point where scratching occurred. When peaks such as that designated as B in FIG. 3 occur on the output chart, the operator of such a test knows to carefully examine the containers to determine if a scratch occurred. If no peaks occur, it is not necessary to further examine the containers. It may be assumed that the coating was satisfactory.

What we claim is:

1. Apparatus for testing a coating applied to glass containers for resistance to scratching when two glass containers are moved relative to one another which comprises, in combination:
    a base;
    a pair of longitudinally spaced-apart support columns mounted on said base;
    a pair of transversely spaced-apart rails extending between and held by said support columns;
    a carriage, slideably mounted on said rails;
    a first container chucking means for holding a first glass container to be tested carried by said carriage, said first container chucking means including;
    a. a support plate attached to said carriage, said support plate having longitudinal slots formed in opposed ends thereof;
    b. a clamp bracket held in one of said slots;
    c. a motor bracket held in the other one of said slots;
    d. a fluid motor, having an extensible operating rod which is directed toward said clamp bracket, secured to said motor bracket;
    e. a clamp pad attached to the end of said extensible operating rod; and
    f. a cradle, generally shaped to conform to the body contours of a glass container to be tested, positioned on said support plate between said clamp bracket and said motor bracket;
    a second container chucking means for holding a second glass container to be tested positioned above said first container chucking means, said second container chucking means including;
    a. a support plate having longitudinal slots formed in opposed ends thereof;
    b. a clamp bracket held in one of said slots;
    c. a motor bracket held in the other one of said slots;
    d. a fluid motor, having an extensible operating rod which is directed toward said clamp bracket, secured to said motor bracket; and
    e. a clamp pad attached to the end of said extensible operating rod;
    a fluid motor, positioned above said second container chucking means, having an extensible operating rod that is attached to said support plate, for applying a downward force on said second chucking means normal to said second chucking means and for supporting said second chucking means;
    support means for holding said fluid motor at a fixed location;
    drive means for moving said carriage along said rails; and
    sensing means for generating a signal quantity representative of the force required to move said carriage.

2. The apparatus of claim 1 which further includes:
    indicating means, responsive to said signal quantity, for displaying the force required to move said carriage.

3. The apparatus of claim 1 wherein said means for moving said carriage includes:
    a drive block slideably mounted on said rails;
    a threaded shaft, threadably engaged with one of said support columns and attached to said drive block, said drive block being located intermediate said carriage and said threaded shaft;
    a motor; and
    gear means connecting said motor to said threaded shaft, whereby said motor will cause rotation of said threaded shaft thereby moving said drive block along said rails.

4. The apparatus of claim 3 wherein said sensing means comprises:
    a load cell, positioned between said carriage and said drive block.

5. The apparatus of claim 3 which further includes:
    a pair of longitudinally spaced-apart switches mounted parallel to said threaded shaft;
    a motor control circuit connected to said motor and said switches and responsive to actuation of said switches to turn said motor off; and
    a switch activator carried by said threaded shaft and positioned to activate said switches when in proximity to said switches.

6. A method for testing scratch resistance coatings placed on glass containers which comprises the steps of:
    placing two coated glass containers in contact with one another;
    applying a known force normal to said contacting glass containers;
    moving said glass containers relative to one another while maintaining contact and said known force;
    sensing the force required to move said glass containers relative to one another, whereby a change in the sensed force indicates scratching of at least one of the coatings;
    generating a signal quantity representative of said sensed force;
    sensing attainment of a pre-selected amount of relative movement of said glass containers; and
    ceasing movement of said glass containers in response to said sensing.

* * * * *